(12) United States Patent
Han et al.

(10) Patent No.: US 6,927,038 B2
(45) Date of Patent: Aug. 9, 2005

(54) TOTAL CYSTEINE ASSAY

(75) Inventors: Qinghong Han, San Diego, CA (US); Mingxu Xu, La Jolla, CA (US); Li Tang, San Diego, CA (US); Yuying Tan, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 147 days.

(21) Appl. No.: 10/301,531

(22) Filed: Nov. 20, 2002

(65) Prior Publication Data
US 2003/0162239 A1 Aug. 28, 2003

Related U.S. Application Data

(60) Provisional application No. 60/333,532, filed on Nov. 20, 2001.

(51) Int. Cl.[7] ............................. C12Q 1/34; C12Q 3/00; G01N 33/53
(52) U.S. Cl. .............................. 435/18; 435/4; 435/975
(58) Field of Search .............................. 435/18, 4, 975

(56) References Cited

U.S. PATENT DOCUMENTS

| 5,985,540 A | 11/1999 | Tan et al. ........................ 435/4 |
| 5,998,191 A | 12/1999 | Tan et al. ..................... 435/232 |
| 6,066,467 A | 5/2000 | Xu et al. ........................ 435/23 |
| 6,265,220 B1 | 7/2001 | Ullman ........................ 436/86 |
| 6,468,762 B1 | 10/2002 | Tan .............................. 435/24 |
| 2002/0123088 A1 | 9/2002 | Matsuyama et al. ........... 435/18 |

FOREIGN PATENT DOCUMENTS

| JP | 2000-270895 | 10/2000 |
| JP | 2000-338096 | 12/2000 |
| WO | WO 98/007872 | 2/1998 |
| WO | WO 01/077670 | 10/2001 |

OTHER PUBLICATIONS

English Language Translation of JP 2000–270895A (Ebinuma et al.) Oct. 3, 3000, Japanese Version provided by Applican Machine Translation provided by Japanese Patent Office Web Site, Oct. 5, 2004, pp. 1–8.*
Han et al., Protein Expression and Purification (1998) 14(2):267–274.
Supplementary European Search Report for EP 02 78 4538, mailed on Nov. 15, 2004, 3 pages.
Tanaka et al., Agricultural and Biological Chemistry (1981) 45(4):1021–1022.
Han et al., Protein Expression & Purification (1998) 14:267–274.
Tan et al., Protein Expression & Purification (1997) 9:233–245.
El–Khairy et al., "Plasma Total Cysteine as a Risk Factor for Vascular Disease. The European Concerted Action Project" Circulation 103:2544–2549 (2001).
Horton et al., "Relationships Among Plasma Homocysteine, Cysteine, and Albumin Concentrations: Potential Utility of Assessing the Cysteine Homocysteine Ratio" J. Clin. Chem. 47:1121–1124 (2001).
Mansoor et al., "Redox Status and Protein Binding of Plasma Aminothiols During the Transient Hyperhomocysteinemia That Follows Homocysteine Administration" Clin. Chem. 39:980–985 (1993).

* cited by examiner

Primary Examiner—Michael Meller
Assistant Examiner—Jennifer Ione Harle
(74) Attorney, Agent, or Firm—Morrison & Foerster LLP

(57) ABSTRACT

A method to determine a total cysteine in biological fluids utilizes similarly treated portions of the fluid with a homocysteinase and a non-specific desulfurase.

9 Claims, 1 Drawing Sheet

TOTAL CYSTEINE ASSAY

CROSS-REFERENCE TO RELATED APPLICATIONS

This application claims priority under 35 U.S.C. § 119 to provisional application 60/333,532 filed 20 Nov. 2001. The contents of that application are incorporated herein by reference.

TECHNICAL FIELD

The invention relates to an enzymatic assay for total cysteine in blood or plasma.

BACKGROUND ART

It has become apparent that the total cysteine content in plasma (tCcys) is an important parameter in evaluating the risk of cardiovascular disease. It has been reported that low risk of cardiovascular disease is associated with tCys levels at 250–275 µM whereas a higher risk is associated both with lower levels (<225 µM) and higher levels (>300 µM). El-Khairy, et al., *Circulation* (2001) 2544–2549. The levels of the cysteine homolog, homocysteine (tHcy) are also relevant as the risk of venous thrombosis and myocardial infarction are increased at high levels of homocysteine. Marcucci, et al., *M. J. Clin. Pathol.* (2001) 116:56–60. It appears that the levels of cysteine and homocysteine are interrelated since cysteine is, along with albumin, a covalent carrier of the homocysteine in circulation and cysteine is also a competitor of homocysteine for cellular uptake as well as a homocysteine metabolite via the transsulfuration pathway. Hortin, et al., *J. Clin. Chem.* (2001) 47:1121–1124.

It is also known that individuals with very high levels of homocysteine due to defects in the transsulfuration pathway have low levels of total cysteine. It is estimated that one percent of the population is defective in the enzyme responsible; homozygous deficiency results in homocysteinuria. The ratio of tCys/tHcy will assist in identifying heterozygotes. Boddie, et al., *Metabolism* (1998) 47:207–211.

In addition, total cysteine levels are correlated with age, total cholesterol concentration, diastolic blood pressure and coffee consumption, but unlike homocysteine levels, not smoking status, folate and vitamin intake, heart rate and physical activity. El-Khairy, et al., *Am. J. Clin. Nutr.* (1999) 70:1016–1024. Both tCys and tHcy are associated with renal failure. Mansoor, et al., *Clin. Chem.* (1993) 39:980–985.

Methods to determine total homocysteine enzymatically have also been described, for example, in U.S. Pat. No. 6,468,762 issued 22 Oct. 2002 as well as U.S. Pat. Nos. 6,066,467; 5,998,191; and 5,985,540, the disclosures of which are incorporated herein by reference.

An alternative method of measuring total cysteine is also described in the above mentioned '762 patent wherein the sample to be assayed is treated with a non-specific desulfurase. To measure cysteine directly, S-adenosyl homocysteine hydrolase (SAHH) and adenosine are added to the sample containing a non-specific desulfurase, where the SAHH is present in sufficient quantity to catalyze the conversion of all of the homocysteine in the sample to SAH, thus protecting it from the action of the desulfurase. Thus, only cysteine levels in the sample are measured.

The present invention provides an alternative enzymatic based assay for total cysteine. The availability of both assays permits not only each total homocysteine and total cysteine to be determined, but also the tCys/tHcy ratio.

DISCLOSURE OF THE INVENTION

The invention is directed to determination of total cysteine in biological fluids, preferably plasma, by concomitant or otherwise controlled determination of both total homocysteine and the sum of the concentrations of homocysteine and cysteine. By utilizing an enzyme which is reactive with both homocysteine and cysteine to produce ammonia, hydrogen sulfide, and the respective α-keto-carboxylic acids (α-ketoglutarate or pyruvate) in one reaction vessel and an enzyme which carries out this desulfurase (lyase) reaction only with homocysteine in another reaction vessel, the total cysteine level can be determined by the difference in concentrations. The results are linear in the range of 2 µM-1,000 µM in plasma.

Thus, in one aspect, the invention is directed to a method to determine the total cysteine concentration (tCys) in a biological fluid which method comprises a) treating a first sample of said fluid with a desulfurase which utilizes both homocysteine and cysteine as substrates and measuring the level of at least one product of said desulfurase to determine the sum of the concentrations of cysteine (tCys) and of homocysteine (tHcy);

b) treating a second sample of said biological fluid with a desulfurase that uses homocysteine specifically as a substrate and measuring the level of at least one product to determine the total concentration of homocysteine (tHcy) and c) subtracting the tHcy obtained in step b) from the tCys plus tCys obtained in step a) to obtain total cysteine concentration.

In another aspect, the invention is directed to a kit for determining total cysteine concentration which comprises, in suitable containers, a desulfurase which utilizes both cysteine and homocysteine as a substrate, a desulfurase which utilizes homocysteine specifically as a substrate, and optionally, a reducing agent effective to reduce disulfide bonds, and optionally reagents for detection of at least one product, along with instructions for conducting the assay.

MODES OF CARRYING OUT THE INVENTION

Figure 1:
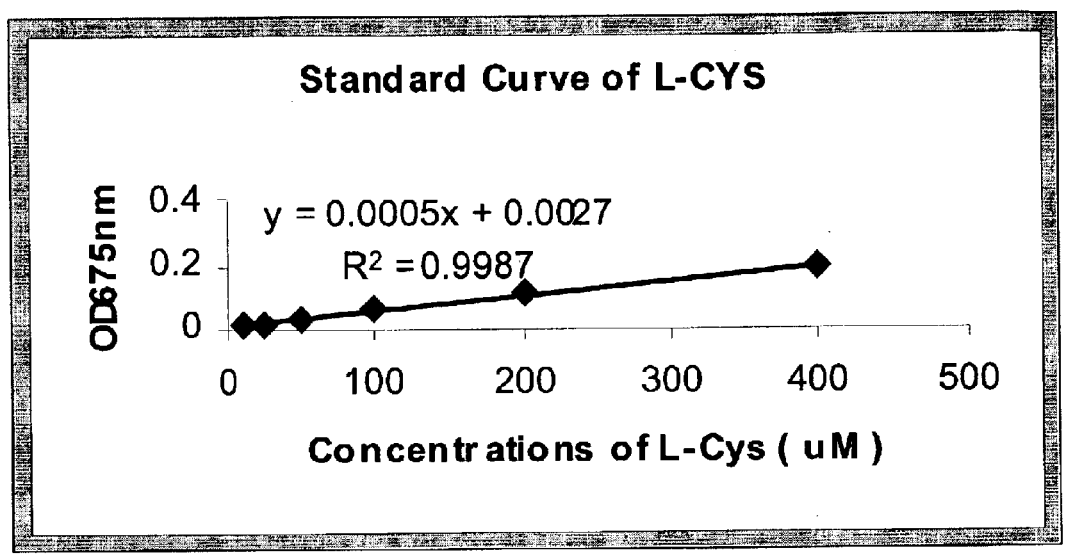
FIG. 1 is a graph showing a typical standard curve of the assay of the invention.

The invention takes advantage of the specificity characteristics of desulfurase enzymes such that the levels of both homocysteine and cysteine can be determined in a biological fluid. Suitable biological fluids include, for example, urine, cerebrospinal fluid, blood and plasma or serum. Much of the literature concerning the significance of these levels relates to plasma or serum. It is usually necessary to treat the sample with a reducing agent that is effective to reduce disulfide bonds (such as dithioerythritol) before the assay is conducted in order to liberate cysteine and homocysteine in their sulfhydryl form so as to be subject to the action of a desulfurase.

The desulfurases useful in the invention convert homocysteine to α-ketoglutarate, ammonia and hydrogen sulfide and may convert cysteine to pyruvate, ammonia and hydrogen sulfide. The assays may involve measurement of any of these products. However, measurement of ammonia or hydrogen sulfide may be more convenient since the same methodology can be employed with respect to the products of both amino acids. The measurement of hydrogen sulfide is particularly preferred, as methods for this measurement are relatively easy. However, means are well known in the art for measurement of α-ketoglutarate, pyruvate, and ammonia and measurement of these products' concentrations could be utilized as well.

One method to conveniently measure the levels of hydrogen sulfide produced is described in the above-referenced U.S. Pat. No. 6,468,762. Briefly, this method involves a first chromogenic reagent which contains an oxidizing agent such as potassium ferricyanide and a second chromogenic reagent which comprises an N,N-dialkyl phenylenediamine. These reagents react with the resulting hydrogen sulfide to form a colored complex which can be measured either spectraphotometrically by absorbance, or, with more sensitivity, by utilizing the fluorescence of the complex. A preferred dialkylphenylenediamine is N,N-dipropyl phenylenediamine (DPPDA) or N,N-dibutyl phenylenediamine (DBPDA).

However, any method of measuring the products of the reaction may be used.

As stated above, one of the desulfurases will utilize both cysteine and homocysteine as a substrate so that when a biological fluid is treated with this desulfurase, after a suitable reaction time, such as 10 minutes or 20 minutes, the desulfurase will have converted both the homocysteine and the cysteine in the biological sample to the above described products. Such enzymes can suitably be prepared from microorganisms. One example is the recombinantly prepared desulfurase from *Pseudomonas putida*. This enzyme is described by Tan, et al., *Protein Purification & Expression* (1997) 9:233–245.

A desulfurase specific for homocysteine, referred to herein as a "homocysteinase" is defined as an enzyme having desulfurase activity with respect to homocysteine as a substrate in preference to cysteine as a substrate such that the amount of hydrogen sulfide liberated from treatment of a sample of blood, urine, tissue fluid, serum, or plasma of a subject with said enzyme is substantially generated from the homocysteine and not from the cysteine in said sample, even when the concentration of homocysteine is ten fold less than the concentration of cysteine in said sample. Alternatively, the homocysteinase has the property that at least about 90% of the hydrogen sulfide produced by action of said homocysteinase upon contacting a biological fluid is contributed by homocysteine, when the concentrations of homocysteine and cysteine in said fluid are, respectively, about 5–15 µM and about 100–300 µM, respectively or wherein at least about 90% of the hydrogen sulfide produced by action of said homocysteinase upon contacting a biological fluid is contributed by homocysteine when the fluid contains 5 µM homocysteine 1,000 µM cysteine. Such homocysteinase enzymes are described in the above-referenced patent; and by Han, et al., *Protein Expression & Purification* (1998) 14:267–274.

As set forth above, the biological fluid is divided into two samples preferably treated identically. Typically, the desulfurase is added to a sample in an amount needed to achieve a final concentration of 0.01–1,000 µg/ml; and reagents are added in amounts needed to achieve final concentrations of 1–100 mM of buffer, more preferably 5–50 mM; 0.01–100 mM reducing agent for disulfide bonds, even more preferably 0.1–10 mM. The nature of the remaining reagents depends on the detection system chosen for the assay.

In one particularly preferred method of detection, the level of products is determined by measuring the concentration or amount of hydrogen sulfide produced. Particularly preferred is the formation of a chromophore which also has the property of being fluorescent. The complex, which is able to absorb light and to fluoresce, is obtained by reaction with N,N-dialkyl phenylenediamine, preferably N,N-dipropyl phenylenediamine (DPPDA) or N,N-dibutyl phenylene diamine (DBPDA). The complex is then oxidized with a suitable oxidizing agent, such as ferric ion in the form of, for example, ferricyanide. While the level of the colored reagent can be measured by absorbance, typically at approximately 670–680 nm, the fluorescence of this complex could be measured by using an excitation wavelength in the range of approximately 665 nm or 640 nm and the measuring corresponding emission at lower wavelengths. The use of fluorescence detection as opposed to absorbance is illustrated below and is shown to enhance the sensitivity of the assay.

The results in the sample containing the non-specific desulfurase provide concentration levels of tHcy plus tCys. The results in the sample containing the homocysteinase provide the concentration of tHcy. Thus, the difference in these concentrations represents the total cysteine concentration in the biological fluid.

The following example is offered to illustrate but not to limit the invention.

EXAMPLE 1

Determination of Cysteine and Homocysteine

Samples to be assayed are divided into two portions: One portion is treated with non-specific desulfurase and the other with homocysteinase.

In each case, 10–20 µl of sample and correspondingly 980–990 µl of Conversion Buffer to a sample total of 1 ml is incubated for 30 minutes at 37° C. The Conversion Buffer is 20 mM potassium phosphate, pH 8.3, 150 mM NaCl, 30 µg/ml, 0.2% Triton X-100, and 1 mm DTT.

The samples are then treated with 10 µl of recombinant homocysteinase or non-specific desulfurase (0.275 mg). The desulfurase is recombinantly produced and is that described by Tan, et al. (supra), isolated from *P. putida*. the homocysteinase is that described by Han, et al. (supra). Both samples are incubated at 37° C. for ten minutes.

The reaction is then stopped by adding 50 µl of chromogen (40 mM N,N-dibutyl-phenylenediamine hydrochloride in 6 M HCl) followed by addition of 50 µl oxidizing agent (40 mM potassium ferricyanide in 20 mM potassium phosphate, pH 8.3). The portions are then incubated for 10 minutes at 37° C. and read by fluorescence with an excitation wavelength of 665 nm and an emission wavelength of 690 nm or by absorbance at 675 nm.

What is claimed is:

1. A method for determining total cysteine concentration (tCys) in a biological fluid sample, which method comprises:

a) determining the total concentration of cysteine plus homocysteine combined (tCys+tHcy) in said sample, by:

contacting a first aliquot of said sample with a non-specific desulfurase under conditions where said desulfurase is capable of degrading both cysteine and homocysteine, allowing said desulfurase to degrade any cysteine and any homocysteine in said first aliquot into a first set of products, determining the concentration of at least one product from said first set of products, where the concentration of the product from said first set of products is interpreted as the total concentration of cysteine plus homocysteine combined (tCys+tHcy);

b) determining the total concentration of homocysteine (tHcy) in said sample, by:

contacting a second aliquot of said sample with a specific homocysteinase under conditions where said homocysteinase is capable of degrading homocysteine without degrading cysteine, allowing said homocysteinase to degrade any homocysteine in said second aliquot into a second set of products, determining the concentration of at least one product from said second set of products, where the concentration of the product from said second set of products is interpreted as the total concentration of homocysteine (tHcy); and c) subtracting the total concentration of homocysteine (tHcy) obtained in step b) from the total concentration of cysteine plus homocysteine combined (tCys+tHcy) obtained in step a) to obtain total cysteine (tCys) concentration.

2. The method of claim 1, wherein the product whose concentration is determined in step a) or in step b) or in both step a) and step b) is hydrogen sulfide.

3. The method of claim 2, wherein the hydrogen sulfide concentration is measured after treating with an oxidizing agent and a dialkyl phenylenediamine.

4. The method of claim 3, wherein the oxidizing agent is ferric ion.

5. The method of claim 1, wherein the product whose concentration is determined in step a) or in step b) or in both step a) and step b) is ammonia.

6. The method of claim 1, wherein the product whose concentration is determined in step a) or in step b) or in both step a) and step b) is a carboxylic acid formed by degradation of cysteine and/or homocysteine.

7. The method of claim 1, wherein the non-specific desulfurase is isolatable from *P. putida*.

8. The method of claim 1, wherein the homocysteinase is isolatable from *T. vaginalis*.

9. The method of claim 1, wherein said biological fluid is serum or plasma.

* * * * *